(12) United States Patent
Chaturvedi et al.

(10) Patent No.: US 6,987,167 B2
(45) Date of Patent: Jan. 17, 2006

(54) PROCESS FOR PRODUCTION OF THE SOMATOSTATIN ANALOG, OCTREOTIDE

(75) Inventors: Nishith C. Chaturvedi, Aurangabad (IN); Suresh Beri, Aurangabad (IN); Ravindra D. Yeole, Aurangabad (IN); Noel J. De Souza, Mumbai (IN)

(73) Assignee: Wockhardt Limited, Mumbai (IN)

( * ) Notice: Subject to any disclaimer, the term of this patent is extended or adjusted under 35 U.S.C. 154(b) by 496 days.

(21) Appl. No.: 10/153,555

(22) Filed: May 22, 2002

(65) Prior Publication Data

US 2004/0225108 A1 Nov. 11, 2004

(51) Int. Cl.
*A61K 38/04* (2006.01)
*C07K 16/00* (2006.01)
*C07K 17/00* (2006.01)
*C07K 5/00* (2006.01)
*C07K 7/00* (2006.01)

(52) U.S. Cl. .................. 530/328; 530/317; 530/333; 424/177

(58) Field of Classification Search ............... 530/328, 530/317, 333; 424/177
See application file for complete search history.

(56) References Cited

U.S. PATENT DOCUMENTS

| | | | | |
|---|---|---|---|---|
| 4,130,554 A | * | 12/1978 | Holly et al. | 530/311 |
| 4,395,403 A | | 7/1983 | Bauer et al. | 424/177 |
| 5,480,870 A | | 1/1996 | Keri et al. | 514/16 |
| 5,723,575 A | * | 3/1998 | Gilon et al. | 530/317 |
| 5,889,146 A | | 3/1999 | Lee et al. | 530/317 |
| 2003/0153494 A1 | * | 8/2003 | Gordon et al. | 514/9 |

FOREIGN PATENT DOCUMENTS

| EP | 0029579 | 6/1981 |
|---|---|---|
| EP | 0953577 | 11/1999 |

OTHER PUBLICATIONS

Alsina, Jordi et al. "Active Carbonate Resins for Solid–Phase Synthesis . . . ", Tetrahedron Letters, vol. 38, No. 5, pp. 883–886, (1997).
Edwards, W. Barry et al. "Generally Applicable, Convenient Solid–Phase Synthesis and Receptor Affinities of Octreotide Analogs". J. Med. Chem. No. 37, (1994) pp. 3749–3757.
Krois, Daniel et al. "Synthesis of N–alpha–(6–hydrazinonicotinoyl)–octreotide:A precursor of a (99mTc) complex." Liebigs Annalen (1996) No. 9 pp 1463–1469.
Arano, Y et al. "Conventional and high yield synthesis of DTPA–conjugated peptides: Application of a monoreactive DTPA to DTPA–D–Phe–octreotide synthesis" Bioconjugate Chem. American Chemical Society (1997) vol. 8 pp 442–446.

* cited by examiner

*Primary Examiner*—Christopher R. Tate
*Assistant Examiner*—Marcela M Cordero Garcia
(74) *Attorney, Agent, or Firm*—Ladas and Parry LLP

(57) ABSTRACT

The present invention relates to a process for commercial production of octreotide using solution peptide chemistry and inexpensive amino acid derivatives. Thus the hexapeptide (Boc) D-Phe-Cys(Acm)-Phe-D-Trp-Lys(Boc)-Thr-OMe is synthesized by condensation of two tripeptide fragments, saponified and condensed with Cys(Acm)-Thr-OL to give the linear octapeptide alcohol. The linear peptide alcohol is treated with iodine, after removal of Boc groups, to give the cyclic peptide octreotide. The linear octapeptide alcohol can alternately be made by condensation of the protected hexapeptide acid with the dipeptide Cys(Acm)-Thr-OMe, followed by reduction with sodium borohydride.

8 Claims, No Drawings

PROCESS FOR PRODUCTION OF THE SOMATOSTATIN ANALOG, OCTREOTIDE

FIELD OF THE INVENTION

The present invention relates to a process for the commercial production of the somatostatin analog, octreotide (I) and its pharmaceutically acceptable salts, using solution peptide chemistry, in high yield and purity.

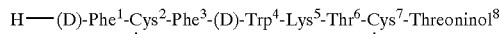
I

The present invention also relates to the intermediate compounds useful in the synthesis of octreotide.

BACKGROUND OF THE INVENTION

Octreotide is a highly potent and pharmacologically selective analog of somatostatin. It inhibits growth hormone for long duration and is therefore indicated for acromegaly to control and reduce the plasma level of growth hormone. The presence of D-Phe at the N-terminal and an amino alcohol at the C-terminal, along with D-tryptophan and a cyclic structure makes it very resistant to metabolic degradation.

The only solution synthesis reported in literature is by Bauer, W. and Pless, J. in Pat. No. U.S. Pat. No. 4,395,403 and EP029579.

Several solid phase syntheses have been subsequently described viz. Patent Nos. EP0953577A1 and U.S. Pat. No. 5,889,146 and in various research publications. Mergler et al (Proceedings of the 12$^{th}$ American Peptide Symposium) have used aminomethyl resin and Fmoc-butyl protection scheme for synthesis of octreotide. Alsina et al. Tetrahedron Letters, 38, 883, 1997) have used an active carbonate resin and Boc-Bzl protection scheme, necessitating the use of hydrogen fluoride/anisole for final deprotection. Edwards et al (J. Med. Chem., 37, 3749, 1994)) have described another synthesis using Fmoc-butyl protection and HMP resin, and Berta et al (EP 0 953 577A1) a synthesis using 2-chlorotrityl-type resin and Fmoc-butyl protection scheme.

All the solid phase syntheses described are useful only for the manufacture of small quantities of octreotide (100–300 mg). These procedures are not suitable for commercial manufacture of octreotide because they use costly resins and costly Fmoc-butyl protected amino acids in 2 to 4 times excess at every step. In one synthesis the final deprotection is carried out with hydrogen fluoride, a destructive and hazardous reagent.

The solution synthesis described by Bauer and Pless in Patent No. U.S. Pat. No. 4,395,403 and EP029579 uses BTFA/TFA to remove the methoxybenzyl group protecting the thiol group of cysteine, followed by cyclization. Decomposition of tryptophan is frequently known to occur during such harsh acid treatment for removal of protecting groups.

SUMMARY OF THE INVENTION

This invention describes a process for obtaining octreotide scalable upwards to kilogram quantities by solution chemistry methods using mild reagents and giving good yields. The process includes the following:

1) Cysteine thiol groups are protected by acetamidomethyl (Acm) groups. Treatment of the Cys(Acm)-containing linear novel octapeptide (XVI) of the invention with iodine, in one step removes the Acm groups and simultaneously effects cyclization to give octreotide (I) in 80–90 percent yield.

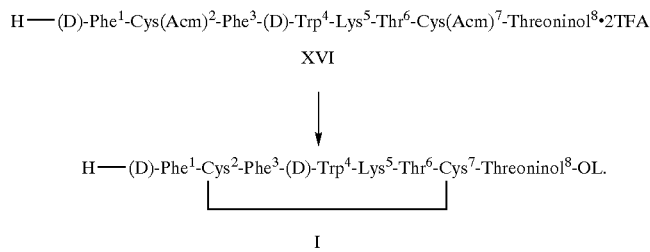

The suitably protected octapeptide alcohol (XVI) of the invention is prepared by either of the following processes.

a) Sodium borohydride reduction of the novel C-terminal dipeptide methyl ester (X) to obtain the dipeptide alcohol (XI) (step 10). The Boc group is removed and the dipeptide (XII) on condensation with the hexapeptide acid (XIV), followed by deprotection, gives the novel intermediate (XVI) (Method 1-Steps 14 and 15)

b) Sodium borohydride reduction of the octapeptide XIX with methyl ester at C-terminal to give the novel intermediate XVI (Method 2-Step 19)

The novel hexapeptide fragment XIV is prepared by condensation of two appropriately protected novel tripeptide fragments V and IX followed by saponification (Steps 12 and 13).

DETAILED DESCRIPTION OF THE INVENTION

The process for the synthesis of

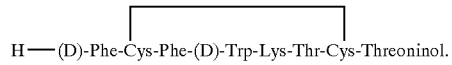

of Formula 1 comprises the synthesis of appropriate peptide fragments using the standard processes of peptide chemistry, known to the practitioners in the art. Thus amino functions of amino acids are protected with one of the commonly employed protecting groups like t-butyloxycarbonyl or benzyloxycarbonyl, and the carboxyl functions of amino acids are protected with alkyl groups like methyl, ethyl, or aralkyl groups like benzyl.

The condensation of the carboxyl group of the amino protected amino acid with the amino group of carboxyl protected amino acid is typically carried out by dissolving the respective appropriately protected amino acids in approximately equimolar quantities in a nonpolar solvent preferably like tetrahydrofuran, dichloromethane, chloroform, and adding a condensing agent such as N,N-dicyclocarbodiimide (DCCI), 1-hydroxybenzotriazole (HOBt) or Benzotriazole-1-yl-oxy-tris-(dimethylamino)-phosphonium hexafluorophosphate (BOP) in approximately equimolar quantity at a temperature of −10° C. to +10° C. and stirring at 20° C.–30° C. for 4 to 24 hrs.

Alternately the carboxyl function of the amino protected aminoacid is activated as mixed anhydride by addition of an alkylchloroformates wherein alkyl means methyl, ethyl, propyl, etc, preferably isobutylchloroformate, a tertiary amine such as TEA, DIEA, NMM, preferably NMM, in approximately equimolar quantities in a nonpolar solvent like dichloromethane, THF, chloroform, preferably THF at a temperature of −10° C. to +10° C. following by addition of carboxyl protected amino acid carrying a free amino group and stirring at 20° C.–30° C. for 4 to 24 hrs. The amino or the carboxyl protecting group is then selectively removed by the use of appropriate deprotecting agents known to those skilled in the art and condensed as desired with another amino acid derivative in an iterative procedure until the desired sequence is obtained.

The basic difference from other procedures already described is that a) the cysteine thiol groups are protected by acetamidomethyl (Acm) groups, b) the N-terminal hexapeptide has been synthesized by condensation of two tripeptide fragments, c) the C-terminal dipeptide alcohol is generated by sodium borohydride reduction of dipeptide methyl ester X instead of using threoninol as the starting material, d) treatment of the linear octapeptide alcohol XVI of the invention with iodine, in one step, removes the Acm groups and simultaneously effects cyclization to give octreotide in good yield, and e) the key intermediate octapeptide alcohol XVI could also be prepared by sodium borohydride reduction of octapeptide methyl ester XIX.

The Process for Producing OCTREOTIDE

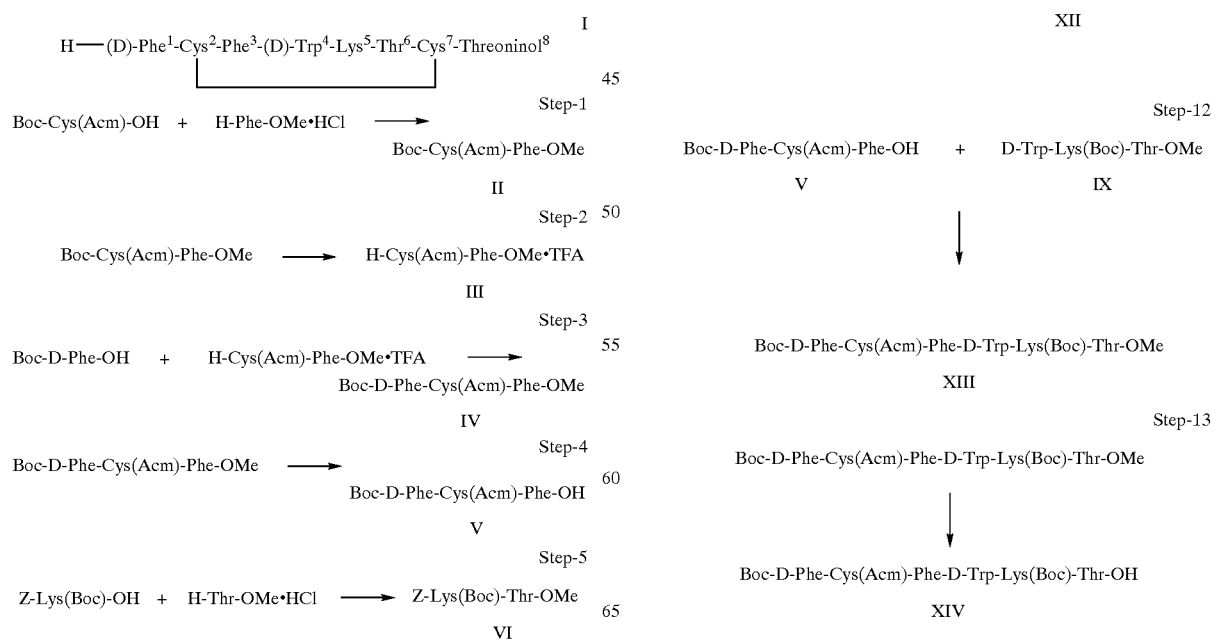

Preparation of Novel Linear Octapeptide Alcohol Di Trifluoroacetate XVI
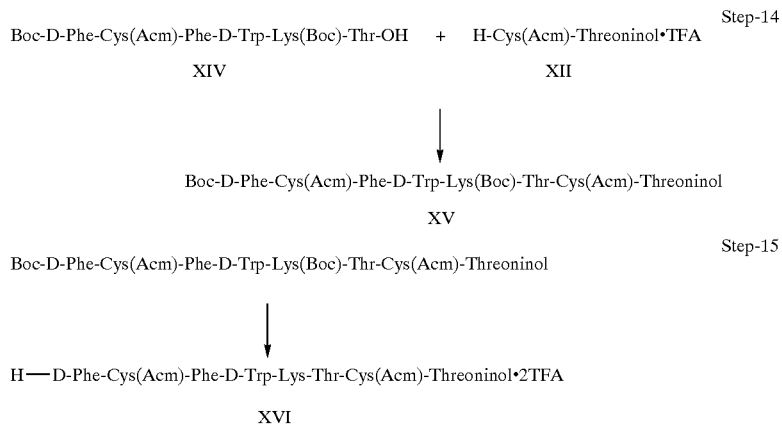
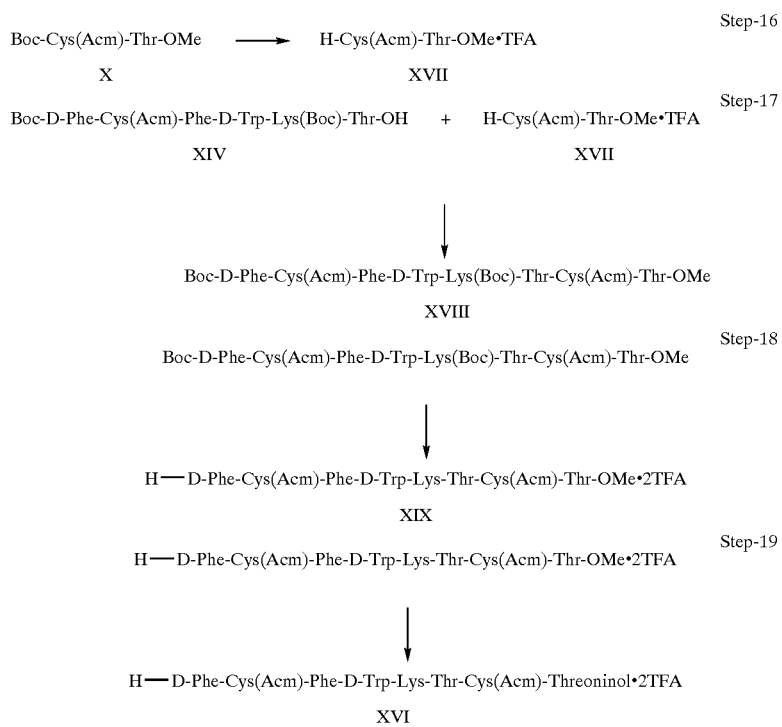
Preparation of Octreotide from Novel Linear Octapeptide Alcohol Di Trifluoroacetate XVI
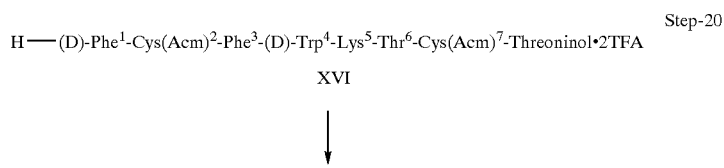

-continued

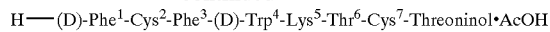
H—(D)-Phe$^1$-Cys$^2$-Phe$^3$-(D)-Trp$^4$-Lys$^5$-Thr$^6$-Cys$^7$-Threoninol·AcOH Abbreviations:
Acm=Acetamidomethyl
Boc=tert.-Butyloxycarbonyl
Bzl=Benzyl
BTFA=Boron-tris-trifluoroacetate
tBu=tert-Butyl
DCCI=Dicyclohexylcarbodiimide
DCM=Dichloromethane
DIEA=Diisopropylethylamine
DMAc=Dimethylacetamide
DMSO=Dimethylsulfoxide
ESMS=Electrospray Mass Spectrometry
EtOH=Ethanol
Fmoc=Flourenylmethoxycarbonyl
HF=Hydrogen fluoride
HOBt=1-Hydroxybenzotriazole
IBCF=Isobutylchloroformate
NMM=N-methylmorpholine
TEA=Triethylamine
TFA=Trifluoroacetic acid
THF=Tetrahydrofuran
Trt=Triphenyl methyl (Trityl)
Z=Benzyloxycarbonyl The following preferred embodiment is described. As shown in step 9, cysteine carrying Boc group for $N^\alpha$ and Acm group for side chain SH protection may be treated with IBCF, NMM, H-Thr-OMe.HCl and TEA, all in approximately equimolar amounts in THF at −10° C. to give dipeptide methyl ester X. The C-terminal methyl ester is converted into alcohol function by reduction with sodium borohydride (2 equivalents) in 90% EtOH at 0° C. to give dipeptide alcohol XI (step 10). The Boc group is removed by treatment with TFA at 0° C. and the resultant compound XII is condensed with appropriately protected hexapeptide XIV, using DCC/HOBt as the condensing agents, in approximately equimolar amounts in THF/DMAc at 0° C., to give the protected octapeptide alcohol XV (step 14). Boc groups are removed by treatment with TFA at 0° C. to give the novel octapeptide alcohol XVI (step 15) which is cyclised with iodine (5–10 equivalents) in 90% MeOH to give octreotide I (Step 20).

Alternately as shown in step 17 (method 2) Boc protection is removed from dipeptide methyl ester X by treatment with TFA at 0° C. and the resulting t dipeptide ester XVII is condensed with the hexapeptide XIV, using DCC/HOBt as the condensation agents in approximately equimolar amounts in THF at 0° C., to give the protected octapeptide methyl ester XVIII. Boc groups are removed by treatment with TFA at 0° C. and the octapeptide methyl ester XIX on reduction with sodium borohydride (5 to 6 equivalents), in 90% EtOH gives the novel octapeptide alcohol XVI (see steps 18 and 19) which is cyclized with iodine (5 to 10 equivalents) to octreotide I (Step 20).

The hexapeptide acid XIV of the invention is synthesized by condensation of two appropriately protected tripeptide fragments V and IX followed by saponification as shown in steps 12 and 13.

For synthesis of tripeptide fragment V, cysteine carrying BoG group for $N^\alpha$ and Acm group for side chain SH protection is treated with IBCF, NMM, H-Phe-OMe.HCl and TEA, all in approximately equimolar amounts in THF/DMSO at −10° C. to give dipeptide II (step 1). The Boc group is removed from the protected dipeptide methyl ester II by treatment with TFA at 0° C. to give III (step 2) which on condensation with (D)-phenyl-alanine carrying Boc group as $N^\alpha$ protection and using IBCF and NMM to make the mixed anhydride, in approximately equimolar amounts in THF at −10° C. gives protected tripeptide methyl ester IV (step 3). The saponification of IV gives the protected tripeptide acid V (step 4).

Similarly for synthesis of tripeptide fragment IX, lysine carrying Z and Boc group at $N^\alpha$ and $N^\epsilon$ respectively as protecting groups is treated with IBCF, NMM, H-Thr-OMe.HCl and TEA, all in approximately equimolar amounts in THF/DMSO at −10° C. to give dipeptide VI (step 5). The Z group is removed from dipeptide VI by hydrogenation over Pd/C to give VII (step 6) which on condensation with (D)-tryptophan carrying Z group as $N^\alpha$ protection and using IBCF and NMM in approximately equimolar amounts in THF/DMSO to make the mixed anhydride, at −10° C. gives protected tripeptide methyl ester VIII (step 7). Removal of Z group from VIII by hydrogenation over Pd/C provides the fragment IX (step 8).

The hexapeptide methyl ester XIII is then made by condensing the tripeptide V carrying the free carboxyl function and the tripeptide IX, carrying the free amino function and using DCCI and HQBt as the condensation reagents in approximately equimolar amounts in THF/DMA at 0° C. (step 12). The methyl ester group of XIII is removed by saponification to give the hexapeptide acid XIV (step 13).

EXAMPLES

I
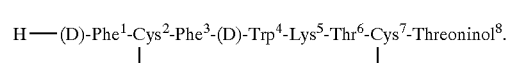
H—(D)-Phe$^1$-Cys$^2$-Phe$^3$-(D)-Trp$^4$-Lys$^5$-Thr$^6$-Cys$^7$-Threoninol$^8$.

A solution of linear octapeptide XVI H-(D)-Phe$^1$-Cys(Acm)$^2$-Phe$^3$-(D)-Trp$^4$-Lys$^5$-Thr$^6$-Cys(Acm)$^7$-Threoninol$^8$·2TFA (5.6 g, 4 mmol) in 90% methanol (200 ml) is added dropwise to a solution of 90% methanol (1 lit) containing iodine (5.0 g, 20 mmol) over a period of an hour at 30°. The stirring is continued at 30° till the completion of reaction. The reaction mixture is cooled to 5° C., 20 ml 1M sodium bisulphite is added followed by the addition of 40 ml 1M sodium hydroxide and 2 ml acetic acid. The solvent is evaporated under vacuum and the crude material is purified by column chromatography to give compound I. Yield 3.7 g (84%), $[\alpha]_D^{20}$=−41.8° (c=1 in 95% acetic acid, Merck Index −42°), ESMS=1019 (M+H).

The novel starting materials which also form an embodiment of this invention may be obtained as follows:

Boc-Cys(Acm)-Phe-OMe (II)

IBCF (13.0 ml, 100 mmol) is added to a solution of Boc-Cys(Acm)-OH (29.2, 100 mmol) and NMM (11.0 ml, 100 mmol) in THF (300 ml) at −10° C. To the reaction mixture is added slowly, after 5 mins, a cold solution of of H-Phe-OMe.HCl (21.5 g, 100 mmol) and TEA (14.0 ml, 100 mmol) in DMSO (10 ml) and THF (50 ml). The stirring is continued at same temperature for one hour and then overnight at 30° C. The solvent is evaporated under vacuum at 40° C. and diluted with ethyl acetate (300 ml). The organic layer is washed with saturated sodium bicarbonate solution (3×100 ml), 0.5M ice cold hydrochloric acid (3×100 ml), brine (3×100 ml), dried on sodium sulphate and evaporated to dryness to give compound II. Yield 43.0 g (94%), m.p.=99° C., $[a]_D^{20}$=−21.7° (c=1 in methanol), ESMS=454.1 (M+H), 476.13 (M+Na).

H-Cys(Acm)-Phe-OMe·TFA (III)

The dipeptide II (40.8 g, 90 mmol) is suspended in DCM (40 ml) and stirred at 0° C. TFA (160 ml) is added and stirring continued for one hour. The TFA and DCM are evaporated under vacuum, ether (200 ml) is added to the residue under stirring, the precipitate filtered, washed with diethyl ether and dried in vacuum to give compound III in 98% yield.
ESMS=354.1 (M+H).

Boc-(D)-Phe-Cys(Acm)-Phe-OMe (IV)

IBCF (11.8 ml, 90 mmol) is added to a solution of Boc-D-Phe-OH (24.0 g, 90 mmol) and NMM (9.9 ml, 90 mmol) in THF (100 ml) at −10° C. To the reaction mixture is added, after 5 mins, a cold solution of compound III (80 mm, 38 g) and TEA (12.7 ml, 80 mmol) in DMSO (25 ml) and THF (50 ml). The stirring is continued for one hour at same temperature and then overnight at 30° C. The reaction mixture is concentrated in vacuum, and the residue is dissolved in ethyl acetate (300 ml). The organic layer is washed with saturated sodium bicarbonate solution (3×100 ml), 0.5M ice cold hydrochloric acid (3×100 ml), brine (3×100 ml), dried on sodium sulphate and evaporated to dryness to give compound IV. Yield 48.8 g (90%), m.p.=134–135° C., $[\alpha]_D^{20}$=−31.6° (c=0.5 in methanol), ESMS=601 (M+H).

Boc-(D)-Phe-Cys(Acm)-Phe-OH (V)

1M sodium hydroxide solution (80.0 ml) is added in 15 minutes to the cold solution of tripeptide methyl ester IV (48.0 g, 80 mmol) dissolved in methanol (300 ml). The solution is stirred at 30° till the completion of reaction. pH is brought to 7 by addition of 1N hydrochloric acid, the solution is concentrated in vacuum, and acidified further with 1M hydrochloric acid (80 ml) under cooling to pH 3, and ethyl acetate (300 ml) is added. The organic layer is separated and water layer is re-extracted with ethyl acetate (200 ml). The organic layers are combined, washed with brine (2×100 ml), dried on sodium sulphate and evaporated to give compound V. Yield 43.5 g (93%), m.p.=141°–145° C., $[\alpha]_D^{20}$=−20.8° (c=1 in methanol), ESMS=587 (M+H).

Z-Lys(Boc)-Thr-OMe (VI)

IBCF (26.0 ml, 200 mmol) is added to a solution of Z-Lys(Boc)-OH (76 g, 200 mmol) and NMM (22.0 ml, 200 mmol) in THF (400 ml) at −10° C. To the reaction mixture is added, after 5 minutes, a cold solution of H-Thr-OMe.HCl (40.6 g, 240 mmol) and TEA (34.0 ml, 240 mmol) in DMSO (50 ml) and THF(100 ml). The stirring is continued at same temperature for an hour and then overnight at 30° C. The solvent is evaporated under vacuum at 40° C. and diluted with ethyl acetate(700 ml). The organic layer is washed with saturated sodium bicarbonate solution(3×100 ml), 0.5M ice cold hydrochloric acid (3×100 ml, brine (3×100 ml), dried on sodium sulphate and evaporated to dryness to give compound VI. Yield 83.0 g (84%), m.p.=77–78° C. $[\alpha]_D^{20}$=−10.2° (c=1 in DMF), ESMS=496 (M+H).

H-Lys(Boc)-Thr-OMe·AcOH (VII)

The dipeptide VI (80.0 g, 160 mmol) is dissolved in methanol (500 ml) and acetic acid (12.0 ml) and hydrogen gas bubbled in the presence of Palladium on carbon (8.0 g, 10%). When the hydrogenation is complete, the solution is filtered through celite bed, evaporated to dryness to yield compound VII in 96% Yield. ESMS=362.1 (M+H).

Z-(D)-Trp-Lys(Boc)-Thr-OMe (VIII)

IBCF (20.8 ml, 160 mmol) is added to a solution of Z-(D)-Trp-OH (54.0 g, 160 mmol) and NMM (17.6 ml, 160 mmol) in THF (400 ml) at −10° C. To the reaction mixture is added, after 5 minutes, a cold solution of compound VII (58 g, 160 mm) and TEA (22.4 ml, 160 mmol) in DMSO (50 ml) and THF(100 ml). The stirring is continued for an hour at same temperature and then overnight at 30° C. The reaction mixture is concentrated in vacuum and the residue is dissolved in ethyl acetate (700 ml). The organic layer is washed with saturated sodium bicarbonate solution (3×100 ml), 0.5M ice cold hydrochloric acid (3×100 ml, brine (3×100 ml), dried on sodium sulphate and evaporated to dryness to give compound VIII. Yield 78 g (70%), m.p.=112–114° C., $[\alpha]_D^{20}$=3.0° (c=1 in DMF), ESMS=682 (M+H).

H-(D)-Trp-Lys(Boc)-Thr-OMe (IX)

The tripeptide VIII (50.0 g, 73 mmol) is dissolved in methanol (500 ml) and hydrogen gas bubbled through in the presence of Palladium on charcoal (6.0 g, 10%). After the hydrogenation is complete, the solution is filtered through celite bed, evaporated to dryness to yield compound IX in 98% yield. ESMS=548 (M+H), 570 (M+Na).

Boc-Cys(Acm)-Thr-OMe (X)

IBCF (39.0 ml, 300 mmol) is added to a solution of Boc-Cys(Acm)-OH (87.6, 300 mmol) and NMM (33.0 ml, 100 mmol) in THF(400 ml) at −10° C. To the reaction mixture is added, after 5 minutes, a cold solution of H-Thr-OMe.HCl (59.3 g, 350 mmol) and (TEA 49.4 ml, 350 mmol) in DMSO (30 ml) and THF (150 ml). The stirring is continued at same temperature for an hour and then overnight at 30° C. The solvent is evaporated under vacuum at 40° C. and diluted with ethyl acetate (700 ml). The organic layer is washed with saturated sodium bicarbonate solution (3×100 ml), 0.5M ice cold hydrochloric acid (3×100 ml), brine (3×100 ml), dried on sodium sulphate and evaporated to dryness to give compound X. Yield 110.0 g (90%), ESMS=408 (M+H).

Boc-Cys(Acm)-Thr-OL (XI)

NaBH$_4$ (7.4 g, 200 mmol) dissolved in 90% ethanol (50 ml) is added dropwise to a solution of compound X (40.7 g, 100 mmol) in 90% ethanol (150 ml) at 0° C. The stirring is continued for 3–4 hours till the reaction is complete as monitored by tlc. The solution is concentrated and desalted by HPLC to give compound XI in 95% yield. ESMS=380 (M+H), 402(M+Na).

H-Cys(Acm)-Thr-OL·TFA     (XII)

The dipeptide XI (7 g, 18 mmol) is dissolved in DCM (10 ml) at 0° C. under stirring. (TFA 30 ml) is added and continue the stirring for an hour. The TFA and DCM are evaporated under vacuum, diethyl ether (100 ml) is added to the residue under stirring, ether is decanted, repeated twice and dried in vacuum to give compound XII in 96% yield. ESMS=280 (M+H), 302 (M+Na).

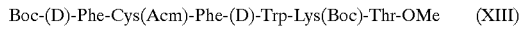
Boc-(D)-Phe-Cys(Acm)-Phe-(D)-Trp-Lys(Boc)-Thr-OMe     (XIII)

The tripeptide acid V (38.0 g, 65 mmol) and HOBt (9.9 g, 65 mmol) is added to a solution of tripeptide IX (35.6 g, 65 mmol) in THF (200 ml) and DMA (30 ml). The solution is cooled to 0° C. and DCCI (13.4 g, 65 mmol) is added. The reaction mixture is stirred at same temperature for 1–2 hours followed by overnight stirring at 30° C. Dicyclohexylurea is filtered, the filtrate is concentrated in vacuum and diluted with (500 ml) ethyl acetate. The organic layer is washed with saturated sodium bicarbonate solution (3×100 ml), 0.5M ice cold hydrochloric acid (3×100 ml), brine (3×100 ml), dried on sodium sulphate and evaporated to dryness to give compound XIII: Yield 55.2 g (76.3%), m.p.=141–143° C., $[\alpha]_D^{20}$=−29.8° (c=1 in in methanol), ESMS=1116 (M+H), 1138(M+Na).

Boc-(D)-Phe-Cys(Acm)-Phe-(D)-Trp-Lys(Boc)-Thr-OH (XIV) 1M sodium hydroxide (45.0 ml) solution is added in 15 minutes to the cold solution of hexapeptide methyl ester XIII (50.2 g, 45 mmol) in methanol (500 ml). The solution is stirred at 30° C. till the reaction is complete. pH is brought to 7 by addition of 1N hydrochloric acid, the solution is concentrated in vacuum, and acidified further with 1M hydrochloric acid (total 45 ml) under cooling to pH 3, and ethyl acetate (300 ml) is added. The organic layer is separated and water layer is re-extracted ethyl acetate (200 ml). The organic layers are combined, washed with brine (2×100 ml), dried on sodium sulphate and evaporated to give title compound XIV. Yield 46.1 g (97%) m.p.=134–135° C., $[\alpha]_D^{20}$=−24.70 (c=1 in methanol), ESMS=1102 (M+1), 1124 (M+Na).

Preparation of Novel Linear Octapeptide Alcohol XVI

Method 1

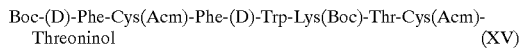
Boc-(D)-Phe-Cys(Acm)-Phe-(D)-Trp-Lys(Boc)-Thr-Cys(Acm)-Threoninol     (XV)

A solution of protected hexapeptide acid XIV (11.0 g, 10 mmol) and HOBt (1.5 g, 10 mmol) in DMAc (30 ml) is added to a solution of dipeptide alcohol TFA salt XII (7.0 g, 18 mmol) and TEA (2.5 ml, 18 mmol) in THF (50 ml) and stirred at 0° C. DCCI (2.2 g, 11 mmol) is added at 0° C. and the reaction mixture is stirred at 0° C. for an hour followed by overnight stirring at 30°. Dicyclohexylurea is filtered and the filtrate concentrated in vacuum followed by addition of diethyl ether (50 ml). The precipitate is filtered, washed with ethyl acetate, chloroform and dried in vacuum to give the title compound XV. Yield 12 g (88%), ESMS=1363.95 (M+H).

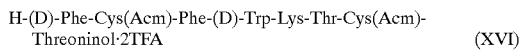
H-(D)-Phe-Cys(Acm)-Phe-(D)-Trp-Lys-Thr-Cys(Acm)-Threoninol·2TFA     (XVI)

The protected octapeptide alcohol XV (16 g) and anisole (2.3 ml) and mercaptoethanol (2.0 ml) are suspended in DCM (20 ml) under N₂. The suspension is cooled to 0° C. and TFA (80 ml) is added. Stirring is continued for one and half hour at same temperature. The TFA and DCM are evaporated under vacuum at 30° C., ether (200 ml) is added to the residue under stirring. The precipitate is filtered, washed with diethyl ether (300 ml), dried in vacuum and purified by HPLC to give compound XVI; Yield 9.7 g (80%), m.p.=161–163° C., $[\alpha]_D^{20}$=−61.2° (c=0.25 in methanol), ESMS=1163 (M+H).

Method 2

H-Cys(Acm)-Thr-OMe·TFA     (XVII)

The dipeptide methyl ester X (8.1 g, 20 mmol) is dissolved in DCM (10 ml) at 0° C. under stirring. TFA (30 ml) is added and continue the stirring for an hour. The TFA and DCM are evaporated under vacuum, diethyl ether (50 ml) is added to the residue under stirring, ether is decanted, repeated twice and dried in vacuum to give compound XVII in 97% yield. ESMS=308 (M+H).

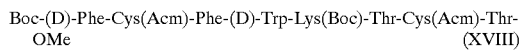
Boc-(D)-Phe-Cys(Acm)-Phe-(D)-Trp-Lys(Boc)-Thr-Cys(Acm)-Thr-OMe     (XVIII)

To a solution of dipeptide XVII (8.1 g, 20 mmol) and TEA (2.8 ml, 20 mmol) in THF (50 ml) is added, hexapeptide acid XIV (11.0 g, 10 mmol) and HOBt (1.5 g, 10 mmol). DCCI (2.2 g, 11 mmol) is added at 0° C. The reaction mixture is stirred at 0° C. for an hour followed by overnight stirring at 30° C. Dicyclohexylurea is filtered and the filtrates are concentrated in vacuum followed by addition of ether (100 ml). The precipitate is filtered, washed with ethyl acetate, water, diethyl ether and dried in vacuum to give the title compound. Yield 11 g (79%). ESMS=1391 (M+H).

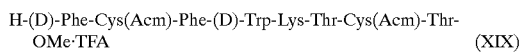
H-(D)-Phe-Cys(Acm)-Phe-(D)-Trp-Lys-Thr-Cys(Acm)-Thr-OMe·TFA     (XIX)

The octapeptide ester XVIII (11 g, 7.9 mm anisole, 2 ml) and mercaptoethanol (2 ml) are suspended in DCM (20 ml) under N₂. The suspension is cooled to 0° C. and TFA (80 ml) is added. Stirring is continued for one and half hour at same temperature. The TFA and DCM are evaporated under vacuum at 30° C., ether (200 ml) is added to the residue under stirring. The precipitates are filtered, washed with diethyl ether (300 ml) and dried in vacuum to give compound XIX: Yield 10.0 g (91%). ESMS=1191 (M+H).

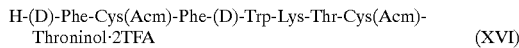
H-(D)-Phe-Cys(Acm)-Phe-(D)-Trp-Lys-Thr-Cys(Acm)-Throninol·2TFA     (XVI)

Sodiumborohydride (1.5 g, 40 mmol) dissolved in 90% ethanol (20 ml) is added dropwise to crude compound XIX (10 g, 7 mm) dissolved in 90% ethanol (50 ml at 0° C. The stirring is continued at same temperature till the reaction is complete. Acetic acid is added to the reaction mixture, which is concentrated and purified on column chromatography to yield compound XVI. Yield 6.8 g (69%), m.p.= 161–163° C., $[\alpha]_D^{20}$=−60.6° (c=0.25 in methanol), ESMS= 1163 (M+H).

What is claimed is:

1. A process for preparing octreotide from linear octapeptide H-D-Phe-Cys(Acm)-Phe-D-Trp-Lys-Thr-Cys(Acm)-Threoninol·2TFA comprising treating H-D-Phe-Cys(Acm)-Phe-D-Trp-Lys-Thr-Cys(Acm)-Threoninol·2TFA (XVI) with iodine under conditions and for a time sufficient to form the octreitide.

2. A process according to claim 1, wherein linear octapeptide H-D-Phe-Cys(Acm)-Phe-D-Trp-Lys-Thr-Cys(Acm)-

Threoninol·2TFA is prepared by condensation of hexapeptide Boc-D-Phe-Cys(Acm)-Phe-D-Trp-Lys(Boc)-Threoninol (XIV) with dipeptide H-Cys(Acm)-Threoninol·TFA (XII) and removing the Boc groups under conditions and for a time sufficient to form the octapeptide.

3. A process according to claim 2, where dipeptide H-Cys(Acm)-Threoninol.TFA (XII) is prepared by reducing Boc-Cys(Acm)-Thr-OMe with sodium borohydride and removing the Boc group under conditions and for a time sufficient to form the dipeptide.

4. A process according to claim 2, wherein hexapeptide Boc-D-Phe-Cys(Acm)-Phe-D-Trp-Lys(Boc)-Thr-OH (XIV) is prepared by condensing of Boc-D-Phe-Cys(Acm)-Phe-OH (V) and H-D-Trp-Lys(Boc)-Thr-OMe (IX) followed by saponification under conditions and for a time sufficient to form the hexapeptide.

5. A process according to claim 4, wherein Boc-D-Phe-Cys(Acm)-Phe-OH (V) is prepared starting from H-Phe-OMe·HCl, and condensing Boc-Cys(Acm) and Boc-D-Phe sequentially through mixed anhydride method, followed by saponification under conditions and for a time sufficient to form Boc-D-Phe-Cys(Acm)-Phe-OH (V).

6. A process according to claim 4, wherein the tripeptide H-D-Trp-Lys(Boc)-Thr-OMe (IX) is prepared starting from H-Thr-OMe·HCl and condensing Z-Lys(Boc) and Z-D-Trp sequentially through mixed anhydride method, where Z is benzyloxycarbonyl followed by removal of Boc group under conditions and for a time sufficient to form the tripeptide.

7. A process according to claim 1, where linear octapeptide H-D-Phe-Cys(Acm)-Phe-D-Trp-Lys-Thr-Cys(Acm)-Threoninol is obtained by condensation of hexapeptide Boc-D-Phe-Cys(Acm)-Phe-D-Trp-Lys(Boc)-Thr-OH with dipeptide H-Cys(Acm)-Threoninol·TFA followed by removal of Boc groups under conditions and for a time sufficient to form the octapeptide.

8. A process according to claim 1, wherein linear octapeotide H-D-Phe-Cys(Acm)-Phe-D-Trp-Lys-Thr-Cys(Acm)-Threoninol is obtained by sodium borohydride reduction of linear octapeptide H-D-Phe-Cys(Acm)-Phe-D-Trp-Lys-Thr-Cys(Acm)-Thr-OMe·2TFA under conditions and for a time sufficient to form the octaoeptide.

* * * * *